US012773533B2

(12) United States Patent
Howell

(10) Patent No.: US 12,773,533 B2
(45) Date of Patent: Oct. 27, 2026

(54) RAPIDLY INSERTABLE CENTRAL CATHETERS INCLUDING CATHETER ASSEMBLIES AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1407 days.

(21) Appl. No.: 17/234,611

(22) Filed: Apr. 19, 2021

(65) Prior Publication Data

US 2021/0322729 A1 Oct. 21, 2021

Related U.S. Application Data

(60) Provisional application No. 63/012,793, filed on Apr. 20, 2020.

(51) Int. Cl.

*A61M 25/06* (2006.01)
*A61B 5/15* (2006.01)
*A61M 25/00* (2006.01)

(52) U.S. Cl.

CPC ... *A61M 25/0606* (2013.01); *A61B 5/150992* (2013.01); *A61M 25/0097* (2013.01); *A61M 25/0026* (2013.01); *A61M 2025/0037* (2013.01)

(58) Field of Classification Search

CPC .......... A61M 25/0606; A61M 25/0097; A61M 25/007; A61B 5/150992

See application file for complete search history.

(56) References Cited

U.S. PATENT DOCUMENTS 1,013,691 A 1/1912 Shields
3,225,762 A 12/1965 Guttman
(Continued)

FOREIGN PATENT DOCUMENTS

DE 60035936 T2 12/2007
DE 202012006191 U1 7/2012
(Continued)

OTHER PUBLICATIONS

PCT/US2021/028018 filed Apr. 19, 2021 International Preliminary Report on Patentability dated Jun. 3, 2022.
(Continued)

*Primary Examiner* — Adam J Eiseman
*Assistant Examiner* — Ari S Padda
(74) *Attorney, Agent, or Firm* — Rutan & Tucker LLP

(57) ABSTRACT

Rapidly insertable central catheters ("RICCs") including catheter assemblies and methods thereof are disclosed. A catheter assembly can include an introducer catheter, an introducer needle, and a RICC. The introducer needle can be disposed in an introducer-catheter lumen of the introducer catheter forming an introducer combination. The RICC can include a catheter tube including an introducing lumen with a number of lumens and a side opening through a side of the catheter tube. The introducing lumen extends from a proximal end of the catheter tube to a distal end of the catheter tube. The side opening opens into the introducing lumen in a distal-end portion of the catheter tube. The introducer combination can be disposed through the side opening, along the distal-end portion of the catheter tube within the introducing lumen, and through the distal end of the catheter tube for introducing the RICC into a blood vessel of a patient.

9 Claims, 3 Drawing Sheets

(56) References Cited

U.S. PATENT DOCUMENTS

| | | | |
|---|---|---|---|
| 3,325,061 | A | 6/1967 | Ellsworth |
| 3,382,872 | A | 5/1968 | Rubin |
| 3,570,485 | A | 3/1971 | Reilly |
| 3,890,976 | A | 6/1975 | Bazell et al. |
| 3,991,762 | A | 11/1976 | Radford |
| 4,205,675 | A | 6/1980 | Vaillancourt |
| 4,292,970 | A | 10/1981 | Hession, Jr. |
| 4,445,893 | A | 5/1984 | Bodicky |
| 4,468,224 | A | 8/1984 | Enzmann et al. |
| 4,484,915 | A | 11/1984 | Tartaglia |
| 4,525,157 | A | 6/1985 | Vaillancourt |
| 4,581,019 | A | 4/1986 | Curelaru et al. |
| 4,582,181 | A | 4/1986 | Samson |
| 4,594,073 | A | 6/1986 | Stine |
| 4,702,735 | A | 10/1987 | Luther et al. |
| 4,743,265 | A | 5/1988 | Whitehouse et al. |
| 4,766,908 | A | 8/1988 | Clement |
| 4,863,432 | A | 9/1989 | Kvalo |
| 4,935,008 | A | 6/1990 | Lewis, Jr. |
| 4,950,252 | A | 8/1990 | Luther et al. |
| 4,957,489 | A | 9/1990 | Cameron et al. |
| 4,994,040 | A | 2/1991 | Cameron et al. |
| 5,017,259 | A | 5/1991 | Kohsai |
| 5,040,548 | A | 8/1991 | Yock |
| 5,057,073 | A | 10/1991 | Martin |
| 5,112,312 | A | 5/1992 | Luther |
| 5,115,816 | A | 5/1992 | Lee |
| 5,120,317 | A | 6/1992 | Luther |
| 5,158,544 | A | 10/1992 | Weinstein |
| 5,167,634 | A | 12/1992 | Corrigan, Jr. et al. |
| 5,188,593 | A | 2/1993 | Martin |
| 5,195,962 | A | 3/1993 | Martin et al. |
| 5,207,650 | A | 5/1993 | Martin |
| RE34,416 | E | 10/1993 | Lemieux |
| 5,267,958 | A | 12/1993 | Buchbinder et al. |
| 5,290,241 | A | 3/1994 | Kraus et al. |
| 5,292,309 | A | 3/1994 | Van Tassel et al. |
| 5,295,970 | A | 3/1994 | Clinton et al. |
| 5,306,247 | A | 4/1994 | Pfenninger |
| 5,312,361 | A | 5/1994 | Zadini et al. |
| 5,322,512 | A | 6/1994 | Mohiuddin |
| 5,328,472 | A | 7/1994 | Steinke et al. |
| 5,350,358 | A | 9/1994 | Martin |
| 5,358,495 | A | 10/1994 | Lynn |
| 5,364,355 | A | 11/1994 | Alden et al. |
| 5,368,567 | A | 11/1994 | Lee |
| 5,378,230 | A | 1/1995 | Mahurkar |
| 5,380,290 | A | 1/1995 | Makower et al. |
| 5,389,087 | A | 2/1995 | Miraki |
| 5,439,449 | A | 8/1995 | Mapes et al. |
| 5,443,457 | A | 8/1995 | Ginn et al. |
| 5,460,185 | A | 10/1995 | Johnson et al. |
| 5,489,271 | A | 2/1996 | Andersen |
| 5,573,520 | A | 11/1996 | Schwartz et al. |
| 5,584,813 | A | 12/1996 | Livingston et al. |
| 5,662,622 | A | 9/1997 | Gore et al. |
| 5,683,370 | A | 11/1997 | Luther et al. |
| 5,713,876 | A | 2/1998 | Bogert et al. |
| 5,718,678 | A | 2/1998 | Fleming, III |
| 5,772,636 | A | 6/1998 | Brimhall et al. |
| 5,885,251 | A | 3/1999 | Luther |
| 5,919,164 | A | 7/1999 | Andersen |
| 5,921,971 | A | 7/1999 | Agro et al. |
| 5,947,940 | A | 9/1999 | Beisel |
| 5,951,518 | A | 9/1999 | Licata et al. |
| 5,957,893 | A | 9/1999 | Luther et al. |
| 5,971,957 | A | 10/1999 | Luther et al. |
| 6,159,198 | A | 12/2000 | Gardeski et al. |
| 6,197,007 | B1 | 3/2001 | Thorne et al. |
| 6,206,849 | B1 | 3/2001 | Martin et al. |
| 6,228,062 | B1 | 5/2001 | Howell et al. |
| 6,273,874 | B1 | 8/2001 | Parris |
| 6,475,187 | B1 | 11/2002 | Gerberding |
| 6,533,782 | B2 | 3/2003 | Howell et al. |
| 6,551,284 | B1 | 4/2003 | Greenberg et al. |
| 6,606,515 | B1 | 8/2003 | Windheuser et al. |
| 6,616,630 | B1 | 9/2003 | Woehr et al. |
| 6,626,868 | B1 | 9/2003 | Prestidge et al. |
| 6,626,869 | B1 | 9/2003 | Bint |
| 6,638,252 | B2 | 10/2003 | Moulton et al. |
| 6,716,228 | B2 | 4/2004 | Tal |
| 6,726,659 | B1 | 4/2004 | Stocking et al. |
| 6,819,951 | B2 | 11/2004 | Patel et al. |
| 6,821,287 | B1 | 11/2004 | Jang |
| 6,926,692 | B2 | 8/2005 | Katoh et al. |
| 6,962,575 | B2 | 11/2005 | Tal |
| 6,991,625 | B1 | 1/2006 | Gately et al. |
| 6,994,693 | B2 | 2/2006 | Tal |
| 6,999,809 | B2 | 2/2006 | Currier et al. |
| 7,025,746 | B2 | 4/2006 | Tal |
| 7,029,467 | B2 | 4/2006 | Currier et al. |
| 7,037,293 | B2 | 5/2006 | Carrillo et al. |
| 7,074,231 | B2 | 7/2006 | Jang |
| 7,094,222 | B1 | 8/2006 | Siekas et al. |
| 7,141,050 | B2 | 11/2006 | Deal et al. |
| 7,144,386 | B2 | 12/2006 | Korkor et al. |
| 7,311,697 | B2 | 12/2007 | Osborne |
| 7,364,566 | B2 | 4/2008 | Elkins et al. |
| 7,377,910 | B2 | 5/2008 | Katoh et al. |
| 7,390,323 | B2 | 6/2008 | Jang |
| D600,793 | S | 9/2009 | Bierman et al. |
| D601,242 | S | 9/2009 | Bierman et al. |
| D601,243 | S | 9/2009 | Bierman et al. |
| 7,594,911 | B2 | 9/2009 | Powers et al. |
| 7,691,093 | B2 | 4/2010 | Brimhall |
| 7,722,567 | B2 | 5/2010 | Tal |
| D617,893 | S | 6/2010 | Bierman et al. |
| D624,643 | S | 9/2010 | Bierman et al. |
| 7,819,889 | B2 | 10/2010 | Healy et al. |
| 7,857,788 | B2 | 12/2010 | Racz |
| D630,729 | S | 1/2011 | Bierman et al. |
| 7,909,797 | B2 | 3/2011 | Kennedy, II et al. |
| 7,909,811 | B2 | 3/2011 | Agro et al. |
| 7,922,696 | B2 | 4/2011 | Tal et al. |
| 7,938,820 | B2 | 5/2011 | Webster et al. |
| 7,967,834 | B2 | 6/2011 | Tal et al. |
| 7,976,511 | B2 | 7/2011 | Fojtik |
| 7,985,204 | B2 | 7/2011 | Katoh et al. |
| 8,073,517 | B1 | 12/2011 | Burchman |
| 8,105,286 | B2 | 1/2012 | Anderson et al. |
| 8,192,402 | B2 | 6/2012 | Anderson et al. |
| 8,202,251 | B2 | 6/2012 | Bierman et al. |
| 8,206,356 | B2 | 6/2012 | Katoh et al. |
| 8,361,011 | B2 | 1/2013 | Mendels |
| 8,372,107 | B2 | 2/2013 | Tupper |
| 8,377,006 | B2 | 2/2013 | Tal et al. |
| 8,454,577 | B2 | 6/2013 | Joergensen et al. |
| 8,585,858 | B2 | 11/2013 | Kronfeld et al. |
| 8,657,790 | B2 | 2/2014 | Tal et al. |
| 8,672,888 | B2 | 3/2014 | Tal |
| 8,696,645 | B2 | 4/2014 | Tal et al. |
| 8,784,362 | B2 | 7/2014 | Boutilette et al. |
| 8,827,958 | B2 | 9/2014 | Bierman et al. |
| 8,876,704 | B2 | 11/2014 | Golden et al. |
| 8,882,713 | B1 | 11/2014 | Call et al. |
| 8,900,192 | B2 | 12/2014 | Anderson et al. |
| 8,900,207 | B2 | 12/2014 | Uretsky |
| 8,915,884 | B2 | 12/2014 | Tal et al. |
| 8,956,327 | B2 | 2/2015 | Bierman et al. |
| 9,023,093 | B2 | 5/2015 | Pal |
| 9,067,023 | B2 | 6/2015 | Bertocci |
| 9,126,012 | B2 | 9/2015 | McKinnon et al. |
| 9,138,252 | B2 | 9/2015 | Bierman et al. |
| 9,180,275 | B2 | 11/2015 | Helm |
| 9,265,920 | B2 | 2/2016 | Rundquist et al. |
| 9,272,121 | B2 | 3/2016 | Piccagli |
| 9,445,734 | B2 | 9/2016 | Grunwald |
| 9,522,254 | B2 | 12/2016 | Belson |
| 9,554,785 | B2 | 1/2017 | Walters et al. |
| 9,566,087 | B2 | 2/2017 | Bierman et al. |
| 9,675,784 | B2 * | 6/2017 | Belson .............. A61M 25/0606 |
| 9,713,695 | B2 | 7/2017 | Bunch et al. |
| 9,764,117 | B2 | 9/2017 | Bierman et al. |
| 9,770,573 | B2 | 9/2017 | Golden et al. |

(56) References Cited

U.S. PATENT DOCUMENTS 9,814,861 B2 11/2017 Boutillette et al.
9,820,845 B2 11/2017 von Lehe et al.
9,861,383 B2 1/2018 Clark
9,872,971 B2 1/2018 Blanchard
9,884,169 B2 2/2018 Bierman et al.
9,889,275 B2 2/2018 Voss et al.
9,913,585 B2 3/2018 McCaffrey et al.
9,913,962 B2 3/2018 Tal et al.
9,981,113 B2 5/2018 Bierman
10,010,312 B2 7/2018 Tegels
10,065,020 B2 9/2018 Gaur
10,086,170 B2 10/2018 Chhikara et al.
10,098,724 B2 10/2018 Adams et al.
10,111,683 B2 10/2018 Tsamir et al.
10,118,020 B2 11/2018 Avneri et al.
10,130,269 B2 11/2018 McCaffrey et al.
10,220,184 B2 3/2019 Clark
10,220,191 B2 3/2019 Belson et al.
10,265,508 B2 4/2019 Baid
10,271,873 B2 4/2019 Steingisser et al.
10,376,675 B2 8/2019 Mitchell et al.
10,675,440 B2 6/2020 Abitabilo et al.
10,688,281 B2 6/2020 Blanchard et al.
10,806,901 B2 10/2020 Burkholz et al.
10,926,060 B2 2/2021 Stern et al.
11,260,206 B2 3/2022 Stone et al.
11,400,260 B2 8/2022 Huang et al.
11,759,607 B1 9/2023 Biancarelli
2002/0040231 A1 4/2002 Wysoki
2002/0045843 A1 4/2002 Barker et al.
2002/0123755 A1 9/2002 Lowe et al.
2002/0198492 A1 12/2002 Miller et al.
2003/0036712 A1 2/2003 Heh et al.
2003/0060863 A1 3/2003 Dobak
2003/0088212 A1 5/2003 Tal
2003/0100849 A1 5/2003 Jang
2003/0153874 A1 8/2003 Tal
2003/0158514 A1 8/2003 Tal
2004/0015138 A1 1/2004 Currier et al.
2004/0049157 A1 3/2004 Plishka et al.
2004/0064086 A1 4/2004 Gottlieb et al.
2004/0092879 A1 5/2004 Kraus et al.
2004/0116864 A1 6/2004 Boudreaux
2004/0116901 A1 6/2004 Appling
2004/0167478 A1 8/2004 Mooney et al.
2004/0193093 A1 9/2004 Desmond
2004/0230178 A1 11/2004 Wu
2005/0004554 A1 1/2005 Osborne
2005/0120523 A1 6/2005 Schweikert
2005/0131343 A1 6/2005 Abrams et al.
2005/0148936 A1 7/2005 Moss
2005/0215956 A1 9/2005 Nerney
2005/0215958 A1 9/2005 Hawthorne
2005/0245882 A1 11/2005 Elkins et al.
2005/0283221 A1 12/2005 Mann et al.
2006/0009740 A1 1/2006 Higgins et al.
2006/0116629 A1 6/2006 Tal et al.
2006/0129100 A1 6/2006 Tal
2006/0129130 A1 6/2006 Tal et al.
2006/0135973 A1 6/2006 Hawkins et al.
2007/0276288 A1 11/2007 Khaw
2008/0045894 A1 2/2008 Perchik et al.
2008/0091137 A1 4/2008 Reavill
2008/0125744 A1 5/2008 Treacy
2008/0125748 A1 5/2008 Patel
2008/0132850 A1 6/2008 Fumiyama et al.
2008/0262430 A1 10/2008 Anderson et al.
2008/0262431 A1 10/2008 Anderson et al.
2008/0294111 A1 11/2008 Tal et al.
2008/0312578 A1 12/2008 DeFonzo et al.
2008/0319387 A1 12/2008 Amisar et al.
2009/0131872 A1 5/2009 Popov
2009/0187147 A1 7/2009 Kurth et al.
2009/0221961 A1 9/2009 Tal et al.
2009/0270889 A1 10/2009 Tal et al.
2009/0292272 A1 11/2009 McKinnon
2010/0030154 A1 2/2010 Duffy
2010/0256487 A1 10/2010 Hawkins et al.
2010/0298839 A1 11/2010 Castro
2010/0305474 A1 12/2010 DeMars et al.
2011/0004162 A1 1/2011 Tal
2011/0009827 A1 1/2011 Bierman et al.
2011/0021994 A1 1/2011 Anderson et al.
2011/0066142 A1 3/2011 Tal et al.
2011/0071502 A1 3/2011 Asai
2011/0144620 A1 6/2011 Tal
2011/0152836 A1 6/2011 Riopelle et al.
2011/0190778 A1 8/2011 Arpasi et al.
2011/0202006 A1 8/2011 Bierman et al.
2011/0230844 A1 9/2011 Shaw et al.
2011/0251559 A1 10/2011 Tal et al.
2011/0270192 A1 11/2011 Anderson et al.
2012/0016346 A1 1/2012 Steinmetz et al.
2012/0041371 A1 2/2012 Tal et al.
2012/0065590 A1 3/2012 Bierman et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0215171 A1 8/2012 Christiansen
2012/0220942 A1 8/2012 Hall et al.
2012/0226239 A1 9/2012 Green
2012/0283640 A1 11/2012 Anderson et al.
2012/0316500 A1 12/2012 Bierman et al.
2013/0046241 A1 2/2013 Okamura et al.
2013/0053763 A1 2/2013 Makino et al.
2013/0053826 A1 2/2013 Shevgoor
2013/0123704 A1 5/2013 Bierman et al.
2013/0158338 A1 6/2013 Kelly et al.
2013/0158506 A1 6/2013 Harris et al.
2013/0188291 A1 7/2013 Vardiman
2013/0237931 A1 9/2013 Tal et al.
2013/0306079 A1 11/2013 Tracy
2014/0025036 A1 1/2014 Bierman et al.
2014/0081210 A1 3/2014 Bierman et al.
2014/0094774 A1 4/2014 Blanchard
2014/0100552 A1 4/2014 Gallacher et al.
2014/0110296 A1 4/2014 Terzibashian
2014/0171833 A1 6/2014 Matsuno et al.
2014/0188211 A1 7/2014 Roeder et al.
2014/0207052 A1 7/2014 Tal et al.
2014/0207069 A1 7/2014 Bierman et al.
2014/0214005 A1 7/2014 Belson
2014/0221831 A1 8/2014 Kurrus et al.
2014/0257111 A1 9/2014 Yamashita et al.
2014/0276432 A1 9/2014 Bierman et al.
2014/0276599 A1 9/2014 Cully et al.
2014/0364766 A1 12/2014 Devgon et al.
2015/0011834 A1* 1/2015 Ayala ................. A61B 17/0218 29/428
2015/0080939 A1 3/2015 Adams et al.
2015/0094653 A1 4/2015 Pacheco et al.
2015/0112307 A1 4/2015 Margolis
2015/0112310 A1 4/2015 Call et al.
2015/0119806 A1 4/2015 Blanchard et al.
2015/0126930 A1 5/2015 Bierman et al.
2015/0148595 A1 5/2015 Bagwell et al.
2015/0157829 A1 6/2015 Bunch et al.
2015/0190168 A1 7/2015 Bierman et al.
2015/0196210 A1 7/2015 McCaffrey et al.
2015/0224287 A1 8/2015 Bian et al.
2015/0231364 A1 8/2015 Blanchard et al.
2015/0283357 A1* 10/2015 Lampropoulos .. A61M 25/0069 156/308.2
2015/0290431 A1 10/2015 Hall et al.
2015/0297868 A1 10/2015 Tal et al.
2015/0306356 A1 10/2015 Gill
2015/0320969 A1 11/2015 Haslinger et al.
2015/0320977 A1 11/2015 Vitullo et al.
2015/0351793 A1 12/2015 Bierman et al.
2015/0359549 A1 12/2015 Lenker et al.
2015/0359998 A1 12/2015 Carmel et al.
2016/0001046 A1 1/2016 Tietze
2016/0030716 A1 2/2016 Mallin et al.

(56) References Cited

U.S. PATENT DOCUMENTS

2016/0067391 A1 3/2016 Real et al.
2016/0082223 A1 3/2016 Barnell
2016/0114124 A1 4/2016 Tal
2016/0158523 A1 6/2016 Helm
2016/0220786 A1* 8/2016 Mitchell ........... A61M 25/0029
2016/0220811 A1 8/2016 Spotnitz et al.
2016/0242661 A1 8/2016 Fischell et al.
2016/0256101 A1 9/2016 Aharoni et al.
2016/0256667 A1 9/2016 Ribelin et al.
2016/0325073 A1 11/2016 Davies et al.
2016/0331938 A1 11/2016 Blanchard et al.
2016/0338728 A1 11/2016 Tal
2016/0346503 A1 12/2016 Jackson et al.
2017/0028135 A1 2/2017 Fransson et al.
2017/0035990 A1 2/2017 Swift
2017/0072165 A1 3/2017 Lim et al.
2017/0120000 A1 5/2017 Osypka et al.
2017/0120014 A1 5/2017 Harding et al.
2017/0120034 A1 5/2017 Kaczorowski
2017/0128700 A1 5/2017 Roche Rebollo
2017/0156987 A1 6/2017 Babbs et al.
2017/0172653 A1* 6/2017 Urbanski ........... A61B 18/1492
2017/0182293 A1 6/2017 Chhikara et al.
2017/0239443 A1 8/2017 Abitabilo et al.
2017/0259043 A1 9/2017 Chan et al.
2017/0273713 A1 9/2017 Shah et al.
2017/0274182 A1 9/2017 O'Bryan et al.
2017/0296792 A1 10/2017 Ornelas Vargas et al.
2017/0326339 A1 11/2017 Bailey et al.
2017/0361070 A1 12/2017 Hivert
2017/0368255 A1 12/2017 Provost et al.
2018/0001062 A1 1/2018 O'Carrol et al.
2018/0008294 A1 1/2018 Garrison et al.
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1* 6/2018 Chan ................. A61M 25/0606
2018/0214674 A1 8/2018 Ebnet et al.
2018/0229004 A1 8/2018 Blanchard et al.
2018/0296799 A1 10/2018 Horst et al.
2018/0296804 A1 10/2018 Bierman
2018/0310955 A1 11/2018 Lindekugel et al.
2018/0369540 A1 12/2018 Asai
2019/0015646 A1 1/2019 Matlock et al.
2019/0021640 A1 1/2019 Burkholz et al.
2019/0038113 A1 2/2019 Chu
2019/0060616 A1 2/2019 Solomon
2019/0076167 A1 3/2019 Fantuzzi et al.
2019/0076628 A1 3/2019 Anstett
2019/0134349 A1 5/2019 Cohn et al.
2019/0192824 A1 6/2019 Cordeiro et al.
2019/0201665 A1 7/2019 Turpin
2019/0209812 A1 7/2019 Burkholz et al.
2019/0240459 A1 8/2019 Belson
2019/0255294 A1 8/2019 Mitchell et al.
2019/0255298 A1 8/2019 Mitchell et al.
2019/0275303 A1 9/2019 Tran et al.
2019/0276268 A1 9/2019 Akingba
2019/0282788 A1 9/2019 Stone et al.
2019/0321590 A1 10/2019 Burkholz et al.
2019/0351196 A1 11/2019 Ribelin et al.
2020/0001051 A1 1/2020 Huang et al.
2020/0016374 A1 1/2020 Burkholz et al.
2020/0046948 A1 2/2020 Burkholz et al.
2020/0100716 A1 4/2020 Devgon et al.
2020/0129732 A1 4/2020 Vogt et al.
2020/0147349 A1 5/2020 Holt
2020/0197579 A1 6/2020 Chu et al.
2020/0197682 A1 6/2020 Franklin et al.
2020/0197684 A1 6/2020 Wax
2020/0237278 A1 7/2020 Asbaghi
2020/0359995 A1 11/2020 Walsh et al.
2021/0030944 A1 2/2021 Cushen et al.
2021/0060306 A1 3/2021 Kumar
2021/0069471 A1 3/2021 Howell
2021/0085927 A1 3/2021 Howell
2021/0100985 A1 4/2021 Akcay et al.
2021/0113809 A1 4/2021 Howell
2021/0113810 A1 4/2021 Howell
2021/0113816 A1 4/2021 DiCianni
2021/0121661 A1 4/2021 Howell
2021/0121667 A1 4/2021 Howell
2021/0228842 A1 7/2021 Scherich et al.
2021/0228843 A1 7/2021 Howell et al.
2021/0244920 A1 8/2021 Kujawa et al.
2021/0290898 A1 9/2021 Burkholz
2021/0290901 A1 9/2021 Burkholz et al.
2021/0290913 A1 9/2021 Horst et al.
2021/0330941 A1 10/2021 Howell et al.
2021/0330942 A1 10/2021 Howell
2021/0361915 A1 11/2021 Howell et al.
2021/0402149 A1 12/2021 Howell
2021/0402153 A1 12/2021 Howell et al.
2022/0001109 A1 1/2022 Simon
2022/0001138 A1 1/2022 Howell
2022/0032013 A1 2/2022 Howell et al.
2022/0032014 A1 2/2022 Howell et al.
2022/0062528 A1 3/2022 Thornley et al.
2022/0062596 A1 3/2022 Ribelin et al.
2022/0126064 A1 4/2022 Tobin et al.
2022/0193376 A1 6/2022 Spataro et al.
2022/0193377 A1 6/2022 Haymond et al.
2022/0193378 A1 6/2022 Spataro et al.
2022/0203075 A1 6/2022 Murphy
2022/0323723 A1 10/2022 Spataro et al.
2022/0331562 A1 10/2022 Jaros et al.
2022/0331563 A1 10/2022 Papadia
2023/0042898 A1 2/2023 Howell et al.
2023/0096377 A1 3/2023 West et al.
2023/0096740 A1 3/2023 Bechstein et al.
2023/0099654 A1 3/2023 Blanchard et al.
2023/0100482 A1 3/2023 Howell
2023/0101455 A1 3/2023 Howell et al.
2023/0102231 A1 3/2023 Bechstein et al.
2023/0173231 A1 6/2023 Parikh et al.
2023/0233814 A1 7/2023 Howell et al.
2023/0381459 A1 11/2023 Belson et al.
2023/0381481 A1 11/2023 Pizzato
2024/0009427 A1 1/2024 Howell et al.
2024/0050706 A1 2/2024 Howell et al.
2024/0198058 A1 6/2024 Howell et al.
2025/0001136 A1 1/2025 Mitchell et al.
2025/0065083 A1 2/2025 Haymond et al.
2025/0082906 A1 3/2025 Howell et al.
2025/0222237 A1 7/2025 Spataro et al.
2025/0235669 A1 7/2025 Howell

FOREIGN PATENT DOCUMENTS

EP 0653220 A1 5/1995
EP 0730880 A1 9/1996
EP 2061385 A1 5/2009
EP 1458437 B1 3/2010
EP 2248549 A2 11/2010
EP 2319576 A1 5/2011
EP 2366422 A1 9/2011
EP 2486880 A2 8/2012
EP 2486881 A2 8/2012
EP 2486951 A2 8/2012
EP 2512576 A2 10/2012
EP 2152348 B1 2/2015
EP 3473291 A1 4/2019
EP 3093038 B1 5/2019
EP 2260897 B1 9/2019
EP 3693051 A1 8/2020
GB 1273547 A 5/1972
JP 2004248987 A 9/2004
JP 2008054859 A 3/2008
WO 94/21315 A1 9/1994
WO 95/32009 A2 11/1995
WO 98/44979 A1 10/1998
WO 98/53871 A1 12/1998

(56) References Cited

FOREIGN PATENT DOCUMENTS

| | | | |
|---|---|---|---|
| WO | 9857685 | A1 | 12/1998 |
| WO | 99/12600 | A1 | 3/1999 |
| WO | 99/26681 | A1 | 6/1999 |
| WO | 00/06221 | A1 | 2/2000 |
| WO | 0054830 | A1 | 9/2000 |
| WO | 2003008020 | A1 | 1/2003 |
| WO | 2003057272 | A2 | 7/2003 |
| WO | 03/068073 | A1 | 8/2003 |
| WO | 2003066125 | A2 | 8/2003 |
| WO | 2005/096778 | A2 | 10/2005 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011/109792 | A1 | 9/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012/154277 | A1 | 11/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2015077560 | A1 | 5/2015 |
| WO | 2015/168655 | A2 | 11/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016/178974 | A1 | 11/2016 |
| WO | 2016/187063 | A1 | 11/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/050576 | A1 | 3/2019 |
| WO | 2019/146026 | A1 | 8/2019 |
| WO | 2019199734 | A1 | 10/2019 |
| WO | 2020014149 | A1 | 1/2020 |
| WO | 2020069395 | A1 | 4/2020 |
| WO | 2020/109448 | A1 | 6/2020 |
| WO | 2020/113123 | A1 | 6/2020 |
| WO | 2021038041 | A1 | 3/2021 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2021/236950 | A1 | 11/2021 |
| WO | 2021226050 | A1 | 11/2021 |
| WO | 2022/031618 | A1 | 2/2022 |
| WO | 2022/094141 | A1 | 5/2022 |
| WO | 2022/133297 | A1 | 6/2022 |
| WO | 2022-140406 | A1 | 6/2022 |
| WO | 2022/140429 | A1 | 6/2022 |
| WO | 2022/217098 | A1 | 10/2022 |
| WO | 2023014994 | A1 | 2/2023 |
| WO | 2023049498 | A1 | 3/2023 |
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |
| WO | 2023146792 | A1 | 8/2023 |

OTHER PUBLICATIONS

PCT/US2021/064174 filed Dec. 17, 2021 International Search Report and Written Opinion dated May 18, 2022.

PCT/US2021/064642 filed Dec. 21, 2021 International Search Report and Written Opinion dated May 11, 2022.

PCT/US2021/064671 filed Dec. 21, 2021 International Search Report and Written Opinion dated May 27, 2022.

PCT/US2022/024085 filed Apr. 8, 2022 International Search Report and Wirtten Opinion dated Sep. 12, 2022.

U.S. Appl. No. 16/398,020, filed Apr. 29, 2019 Examiner's Answer dated Oct. 31, 2022.

U.S. Appl. No. 17/031,478, filed Sep. 24, 2020 Notice of Allowance dated Sep. 16, 2022.

U.S. Appl. No. 17/156,252, filed Jan. 22, 2021 Non-Final Office Action dated Oct. 25, 2022.

PCT/US2021/039084 filed Jun. 25, 2021 International Search Report and Written Opinion dated Jan. 10, 2022.

PCT/US2021/039843 filed Jun. 30, 2021 International Search Report and Written Opinion dated Nov. 11, 2021.

PCT/US2021/044029 filed Jul. 30, 2021 International Search Report and Written Opinion dated Dec. 9, 2021.

U.S. Appl. No. 16/398,020, filed Apr. 29, 2019 Final Office Action dated Jan. 25, 2022.

U.S. Appl. No. 17/006,553, filed Aug. 28, 2020 Non-Final Office Action dated Mar. 16, 2022.

U.S. Appl. No. 17/077,728, filed Oct. 22, 2020 Non-Final Office Action dated Feb. 9, 2022.

U.S. Appl. No. 16/398,020, filed Apr. 29, 2019 Board Decision dated Oct. 30, 2023.

U.S. Appl. No. 16/398,020, filed Apr. 29, 2019 Non-Final Office Action dated Jan. 18, 2024.

U.S. Appl. No. 17/237,909, filed Apr. 22, 2021 Notice of Allowance dated Oct. 27, 2023.

U.S. Appl. No. 17/240,591, filed Apr. 26, 2021 Final Office Action dated Dec. 6, 2023.

U.S. Appl. No. 17/390,682, filed Jul. 30, 2021 Non-Final Office Action dated Dec. 1, 2023.

U.S. Appl. No. 17/392,061, filed Aug. 2, 2021 Final Office Action dated Nov. 21, 2023.

U.S. Appl. No. 17/513,789, filed Oct. 28, 2021 Non-Final Office Action dated Jan. 9, 2024.

U.S. Appl. No. 17/557,924, filed Dec. 21, 2021 Non-Final Office Action dated Nov. 3, 2023.

PCT/US2022/039614 filed Aug. 5, 2022 International Search Report and Written Opinion dated Dec. 22, 2022.

PCT/US2022/044848 filed Sep. 27, 2022 International Search Report and Written Opinion dated Feb. 3, 2023.

PCT/US2022/044879 filed Sep. 27, 2022 International Search Report and Written Opinion dated Mar. 3, 2023.

PCT/US2022/044901 filed Sep. 27, 2022 International Search Report and Written Opinion dated Mar. 3, 2023.

PCT/US2022/044918 filed Sep. 27, 2022 International Search Report and Written Opinion dated Feb. 21, 2023.

PCT/US2022/044923 filed Sep. 27, 2022 International Search Report and Written Opinion dated Feb. 15, 2023.

U.S. Appl. No. 17/156,252, filed Jan. 22, 2021 Notice of Allowance dated Apr. 24, 2023.

U.S. Appl. No. 17/237,909, filed Apr. 22, 2021 Restriction Requirement dated Feb. 1, 2023.

U.S. Appl. No. 17/326,017, filed May 20, 2021 Non-Final Office Action dated Jan. 26, 2023.

U.S. Appl. No. 17/390,682, filed Jul. 30, 2021 Non-Final Office Action dated Mar. 2, 2023.

(56) References Cited

OTHER PUBLICATIONS

U.S. Appl. No. 17/392,061, filed Aug. 2, 2021 Restriction Requirement dated Mar. 30, 2023.
PCT/US2021/057135 filed Oct. 28, 2021 International Preliminary Report on Patentability dated May 2, 2023.
PCT/US2023/011173 filed Jan. 19, 2023 International Search Report and Written Opinion dated May 22, 2023.
PCT/US2021/057135 filed Oct. 28, 2021 International Search Report and Written Opinion dated Mar. 11, 2022.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/392,061, filed Aug. 2, 2021 Non-Final Office Action dated Jul. 17, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Final Office Action dated Jul. 27, 2023.
U.S. Appl. No. 17/513,789, filed Oct. 28, 2021 Restriction Requirement dated Oct. 3, 2023.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
U.S. Appl. No. 17/031,478, filed Sep. 24, 2020 Non-Final Office Action dated May 11, 2022.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Non-Final Office Action dated May 11, 2021.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
U.S. Appl. No. 16/398,020, filed Apr. 29, 2019 Notice of Allowance dated May 20, 2024.
U.S. Appl. No. 17/240,591, filed Apr. 26, 2021 Advisory Action dated Feb. 22, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Final Office Action dated Mar. 13, 2024.
U.S. Appl. No. 17/360,694, filed Jun. 28, 2021 Non-Final Office Action dated Feb. 14, 2024.
U.S. Appl. No. 17/390,682, filed Jul. 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/392,061, filed Aug. 2, 2021 Advisory Action dated Feb. 14, 2024.
U.S. Appl. No. 17/392,061, filed Aug. 2, 2021 Non-Final Office Action dated Apr. 23, 2024.
U.S. Appl. No. 17/513,789, filed Oct. 28, 2021 Final Office Action dated Jul. 9, 2024.
U.S. Appl. No. 17/554,978, filed Dec. 17, 2021 Non-Final Office Action dated Apr. 19, 2024.
U.S. Appl. No. 17/557,924, filed Dec. 21, 2021 Final Office Action dated Feb. 29, 2024.
U.S. Appl. No. 17/240,591, filed Apr. 26, 2021 Final Office Action dated Aug. 14, 2024.
U.S. Appl. No. 17/358,504, filed Jun. 25, 2021 Notice of Allowance dated Jul. 17, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.
U.S. Appl. No. 17/558,124, filed Dec. 21, 2021 Non-Final Office Action dated Sep. 20, 2024.
U.S. Appl. No. 17/461,619, filed Aug. 30, 2021 Advisory Action dated Aug. 14, 2025.
U.S. Appl. No. 17/461,619, filed Aug. 30, 2021 Final Office Action dated Jun. 2, 2025.
U.S. Appl. No. 17/716,675, filed Apr. 8, 2022 Restriction Requirement dated Jul. 2, 2025.
U.S. Appl. No. 17/882,388, filed Aug. 5, 2022 Non-Final Office Action dated Aug. 20, 2025.
U.S. Appl. No. 17/954,096, filed Sep. 27, 2022 Non-Final Office Action dated Aug. 26, 2025.
U.S. Appl. No. 17/954,132, filed Sep. 27, 2022 Non-Final Office Action dated Aug. 21, 2025.
U.S. Appl. No. 17/392,061, filed Aug. 2, 2021 Notice of Allowance dated Oct. 27, 2025.
U.S. Appl. No. 17/461,619, filed Aug. 30, 2021 Non-Final Office Action dated Oct. 7, 2025.
U.S. Appl. No. 17/716,675, filed Apr. 8, 2022 Non-Final Office Action dated Sep. 11, 2025.
U.S. Appl. No. 17/953,663, filed Sep. 27, 2022 Restriction Requirement dated Oct. 3, 2025.
U.S. Appl. No. 17/953,860, filed Sep. 27, 2022 Restriction Requirement dated Oct. 22, 2025.
U.S. Appl. No. 17/953,959, filed Sep. 27, 2022 Restriction Requirement dated Oct. 22, 2025.
U.S. Appl. No. 18/099,185, filed Jan. 19, 2023 Non-Final Office Action dated Dec. 2, 2025.
U.S. Appl. No. 17/461,619, filed Aug. 30, 2021 Non-Final Office Action dated Feb. 11, 2025.
U.S. Appl. No. 17/513,789, filed Oct. 28, 2021 Notice of Allowance dated Jan. 3, 2025.
U.S. Appl. No. 17/392,061, filed Aug. 2, 2021 Advisory Action dated Mar. 12, 2025.
U.S. Appl. No. 17/392,061, filed Aug. 2, 2021 Non-Final Office Action dated Apr. 5, 2025.
U.S. Appl. No. 17/558,124, filed Dec. 21, 2021 Notice of Allowance dated Mar. 7, 2025.
U.S. Appl. No. 17/240,591, filed Apr. 26, 2021 Board Decision dated Feb. 18, 2026.

(56) References Cited

OTHER PUBLICATIONS

U.S. Appl. No. 17/390,682, filed Jul. 30, 2021 Notice of Allowance dated Dec. 15, 2025.
U.S. Appl. No. 17/882,388, filed Aug. 5, 2022 Final Office Action dated Jan. 12, 2026.
U.S. Appl. No. 17/953,663, filed Sep. 27, 2022 Non-Final Office Action dated Jan. 22, 2026.
U.S. Appl. No. 17/953,860, filed Sep. 27, 2022 Non-Final Office Action dated Jan. 29, 2026.
U.S. Appl. No. 17/954,096, filed Sep. 27, 2022 Final Office Action dated Feb. 10, 2026.
U.S. Appl. No. 17/954,132, filed Sep. 27, 2022 Final Office Action dated Mar. 4, 2026.
U.S. Appl. No. 18/372,610, filed Sep. 25, 2023 Notice of Allowance dated Dec. 16, 2025.
U.S. Appl. No. 18/383,814, filed Oct. 25, 2023 Restriction Requirement dated Jan. 22, 2026.
U.S. Appl. No. 17/240,591, filed Apr. 26, 2021 Notice of Allowance dated Mar. 25, 2026.
U.S. Appl. No. 17/716,675, filed Apr. 8, 2022 Non-Final Office Action dated Mar. 9, 2026.
U.S. Appl. No. 17/882,388, filed Aug. 5, 2022 Notice of Allowance dated Apr. 13, 2026.
U.S. Appl. No. 17/953,663, filed Sep. 27, 2022 Notice of Allowance dated May 14, 2026.
U.S. Appl. No. 17/953,860, filed Sep. 27, 2022 Final Office Action dated May 20, 2026.
U.S. Appl. No. 17/953,959, filed Sep. 27, 2022 Non-Final Office Action dated Mar. 30, 2026.
U.S. Appl. No. 17/954,096, filed Sep. 27, 2022 Notice of Allowance dated Apr. 23, 2026.
U.S. Appl. No. 18/075,261, filed Dec. 5, 2022 Non-Final Office Action dated Apr. 22, 2026.
U.S. Appl. No. 18/099,185 filed Jan. 19, 2023 Final Office Action dated Apr. 20, 2026.
U.S. Appl. No. 18/383,814, filed Oct. 25, 2023 Non-Final Office Action dated Apr. 17, 2026.
U.S. Appl. No. 18/593,431, filed Mar. 1, 2024 Non-Final Office Action dated Apr. 21, 2026.

* cited by examiner

RAPIDLY INSERTABLE CENTRAL CATHETERS INCLUDING CATHETER ASSEMBLIES AND METHODS THEREOF

PRIORITY

This application claims the benefit of priority to U.S. Patent Application No. 63/012,793, filed Apr. 20, 2020, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs") and methods thereof that address the foregoing.

SUMMARY

Disclosed herein is a method for inserting a RICC into a blood-vessel lumen of a patient including, in some embodiments, a catheter assembly-obtaining step, a needle tract-establishing step, an introducer needle-removing step, an introducer catheter-advancing step, and a RICC-advancing step. The catheter assembly-obtaining step includes obtaining a catheter assembly including an introducer combination and the RICC. The introducer combination includes an introducer needle disposed in an introducer-catheter lumen of an introducer catheter. The RICC includes a catheter tube with an introducing lumen and a side opening through a side of the catheter tube that opens into the introducing lumen. The introducer combination is disposed through the side opening, along a distal-end portion of the catheter tube within the introducing lumen, and through a distal end of the catheter tube. The needle tract-establishing step includes establishing a needle tract with a tip of the introducer needle. The needle tract extends from an area of skin to the blood-vessel lumen of the patient. The introducer needle-removing step includes removing the introducer needle from the introducer combination and leaving the introducer catheter in place. The introducer catheter-advancing step includes advancing the introducer catheter into the blood-vessel lumen. The RICC-advancing step includes advancing the RICC into the blood-vessel lumen over the introducer catheter until a distal end of the RICC is commensurate with a distal end of the introducer catheter, the RICC is pushed off the introducer catheter, or the distal end of the RICC is past the distal end of the introducer catheter but not pushed off the introducer catheter.

In some embodiments, the method further includes an introducer combination-disposing step of disposing the introducer combination in the side opening of the catheter tube.

In some embodiments, the method further includes an introducer combination-adjusting step and needle tip-ensuring step. The introducer combination-adjusting step includes adjusting the introducer combination such that at least about 1-7 cm of the introducer combination extends from the distal end of the RICC. The needle tip-ensuring step includes ensuring the tip of the introducer needle extends past the distal end of the introducer catheter before establishing the needle tract.

In some embodiments, the method further includes a blood-aspirating step of aspirating blood with a syringe fluidly connected to the introducer needle. The blood-aspirating step confirms the tip of the introducer needle is disposed in the blood-vessel lumen before removing the introducer needle from the introducer combination.

In some embodiments, introducer catheter-advancing step includes advancing the introducer catheter at least about 1-7 cm into the blood-vessel lumen. Advancing the introducer catheter at least about 1-7 cm into the blood-vessel lumen ensures the introducer catheter is sufficiently disposed in the blood-vessel lumen before the RICC-advancing step.

In some embodiments, the RICC is advanced into the blood-vessel lumen over the introducer catheter until the distal end of the RICC is commensurate with the distal end of the introducer catheter or the distal end of the RICC is past the distal end of the introducer catheter but not pushed off the introducer catheter in the RICC-advancing step.

In some embodiments, the method further includes an introducer catheter-removing step of removing the introducer catheter from the RICC through the side opening through the side of the catheter tube.

In some embodiments, advancing the RICC into the blood-vessel lumen over the introducer catheter until the RICC is pushed off the introducer catheter in the RICC-advancing step simultaneously removes the introducer catheter from the RICC through the side opening through the side of the catheter tube.

Also disclosed herein is a RICC including, in some embodiments, a catheter tube, a hub, and a number of extension legs extending from the hub. The catheter tube includes an introducing lumen of a number of catheter-tube lumens and a side opening through a side of the catheter tube. The introducing lumen extends from a proximal end of the catheter tube to a distal end of the catheter tube. The side opening opens into the introducing lumen in a distal-end portion of the catheter tube. The catheter tube is configured to accommodate an introducer needle, an introducer catheter, or a combination thereof through the side opening, along the distal-end portion of the catheter tube within the introducing lumen, and through the distal end of the catheter tube for introducing the RICC into a blood vessel of a patient. The hub is coupled to a proximal-end portion of the catheter tube. The hub includes a number of hub lumens equal in number to the number of catheter-tube lumens. The number of extension legs extending from the hub is equal in number to the number of catheter-tube lumens. Each extension leg of the number of extension legs includes an extension-leg lumen.

In some embodiments, the side opening is configured to seal when the introducer needle, the introducer catheter, or the combination thereof is removed from the RICC.

In some embodiments, the side opening is a puncture established by the introducer needle, the introducer catheter, or the combination thereof. The catheter tube around at least the puncture is formed of an elastomeric material configured to return to its default state when the introducer needle, the introducer catheter, or the combination thereof is removed from the puncture. The catheter tube around the puncture seals the puncture when returning to the default state.

In some embodiments, the catheter tube includes a flap over the side opening, extending into the side opening, or both configured to be held open by the introducer needle, the introducer catheter, or the combination thereof. The flap is configured to return to its default state when the introducer needle, the introducer catheter, or the combination thereof is removed from the side opening. The flap seals the side opening when returning to the default state.

In some embodiments, the catheter tube includes an area of reinforcement about the side opening. The area of reinforcement is configured to maintain an integrity of the catheter tube about the side opening.

In some embodiments, the number of catheter-tube lumens, the number of hub lumens, and a number of extension-leg lumens is three. The RICC includes a set of three lumens including a distal lumen, a medial lumen, and a proximal lumen. The set of three lumens is formed of fluidly connected portions of the catheter-tube lumens, the hub lumens, and the extension-leg lumens.

In some embodiments, the distal lumen has a distal-lumen opening in a distal end of the RICC. The medial lumen has a medial-lumen opening in the side of the catheter tube distal of the side opening. The proximal lumen has a proximal-lumen opening in the side of the catheter tube distal of the side opening but proximal of the medial-lumen opening.

Also disclosed herein is a catheter assembly including, in some embodiments, an introducer catheter, an introducer needle, and a RICC. The introducer needle is disposed in an introducer-catheter lumen of the introducer catheter forming an introducer combination. The RICC includes a catheter tube including an introducing lumen of a number of catheter-tube lumens and a side opening through a side of the catheter tube. The introducing lumen extends from a proximal end of the catheter tube to a distal end of the catheter tube. The side opening opens into the introducing lumen in a distal-end portion of the catheter tube. The introducer combination is disposed through the side opening, along the distal-end portion of the catheter tube within the introducing lumen, and through the distal end of the catheter tube for introducing the RICC into a blood vessel of a patient.

In some embodiments, the catheter assembly further includes a syringe. The syringe includes a tip extending from a barrel of the syringe. The tip is configured as a Luer connector for connecting to a hub of the introducer needle, which hub is configured as a complementary Luer connector.

In some embodiments, the side opening is configured to seal when the introducer catheter is removed from the RICC.

In some embodiments, the side opening is a puncture established by the introducer needle. The catheter tube around at least the puncture is formed of an elastomeric material configured to return to its default state when the introducer catheter is removed from the puncture. The catheter tube around the puncture seals the puncture when returning to the default state.

In some embodiments, the catheter tube includes a flap over the side opening, extending into the side opening, or both configured to be held open by the introducer catheter. The flap is configured to return to its default state when the introducer catheter is removed from the side opening. The flap seals the side opening when returning to the default state.

In some embodiments, the catheter tube includes an area of reinforcement about the side opening. The area of reinforcement is configured to maintain an integrity of the catheter tube about the side opening.

In some embodiments, the RICC further includes a hub and a number of extension legs extending from the hub. The hub is coupled to a proximal-end portion of the catheter tube. The hub includes a number of hub lumens equal in number to the number of catheter-tube lumens. The number of extension legs extending from the hub is equal in number to the number of catheter-tube lumens. Each extension leg of the number of extension legs includes an extension-leg lumen.

In some embodiments, the number of catheter-tube lumens, the number of hub lumens, and a number of extension-leg lumens is three. The RICC includes a set of three lumens including a distal lumen, a medial lumen, and a proximal lumen. The set of three lumens is formed of fluidly connected portions of the catheter-tube lumens, the hub lumens, and the extension-leg lumens.

In some embodiments, the distal lumen has a distal-lumen opening in a distal end of the RICC. The medial lumen has a medial-lumen opening in the side of the catheter tube distal of the side opening. The proximal lumen has a proximal-lumen opening in the side of the catheter tube distal of the side opening but proximal of the medial-lumen opening.

These and other features of the concepts provided herein will become more apparent to those of skill in the art in view of the accompanying drawings and following description, which describe particular embodiments of such concepts in greater detail.

DRAWINGS

DESCRIPTION

Figure 1:
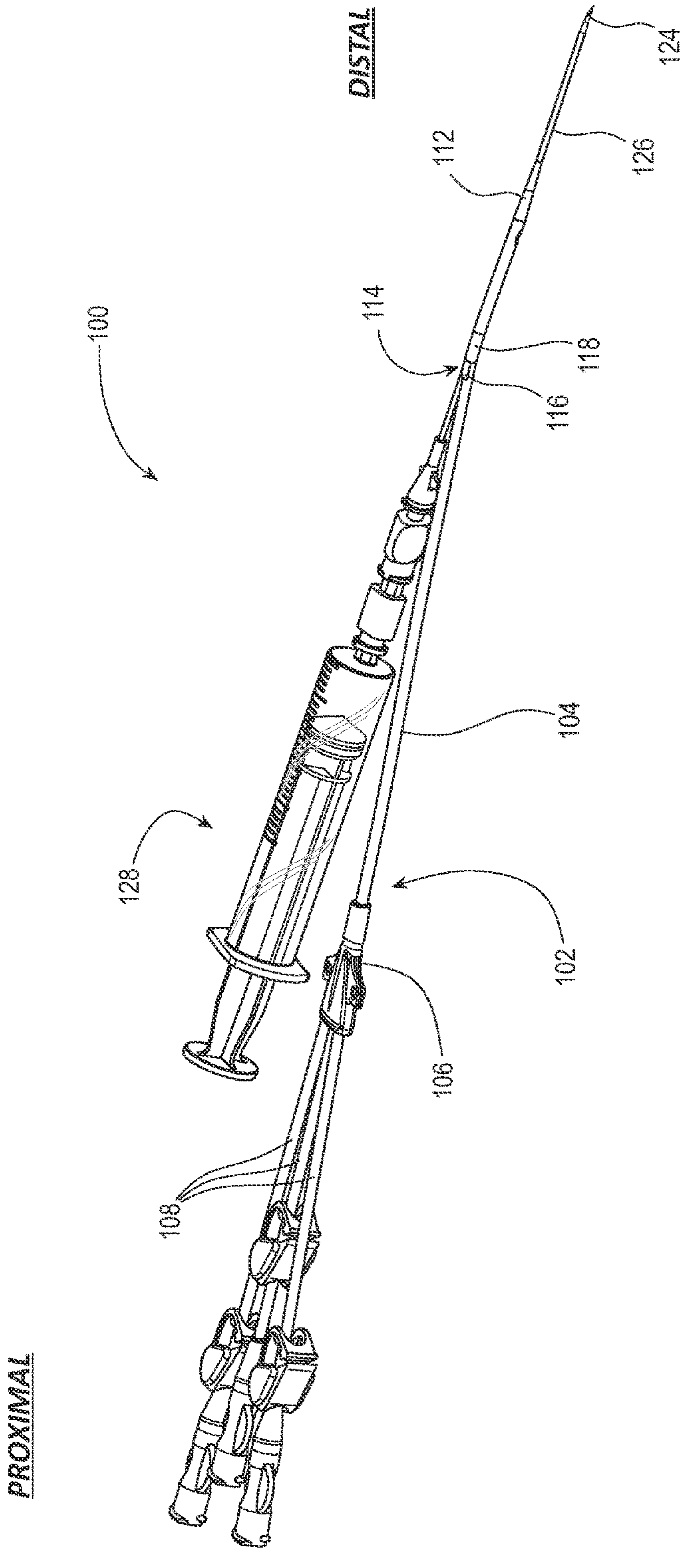
FIG. 1 illustrates a view of a catheter assembly including a RICC in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

With respect to "a number of" features or steps, the number of features or steps includes one or more features or steps. For example, a number of catheter-tube lumens of a catheter tube is intended to be one or more catheter-tube lumens of the catheter tube. Likewise, a number of extension legs of a catheter is intended to be one or more extension legs of the catheter.

Unless defined otherwise, all technical and scientific terms used herein have the same meaning as commonly understood by those of ordinary skill in the art.

As set forth above, there is a need to reduce the number of steps and medical devices involved in introducing a catheter such as a CVC into a patient and advancing the catheter through a vasculature thereof. Disclosed herein are RICCs and methods thereof that address the foregoing.

Rapidly Insertable Central Catheters

Figure 2:
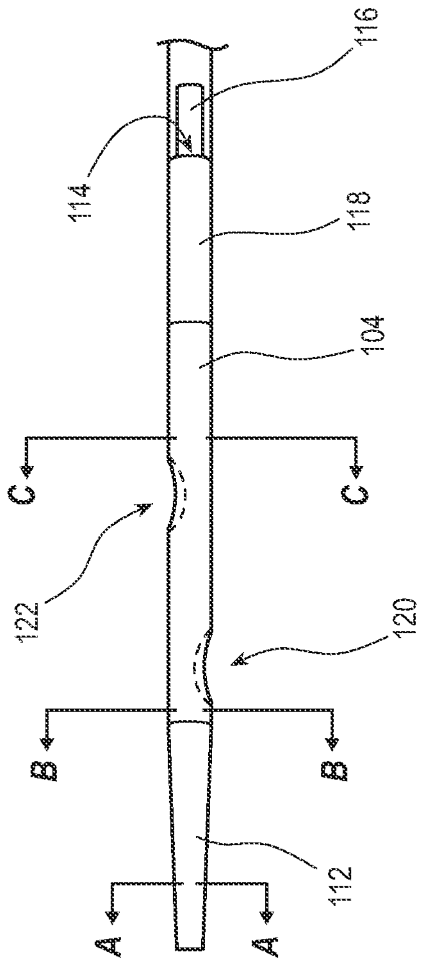
FIG. 2 illustrates a distal portion of a catheter tube of the RICC in accordance with some embodiments.
Figure 4:
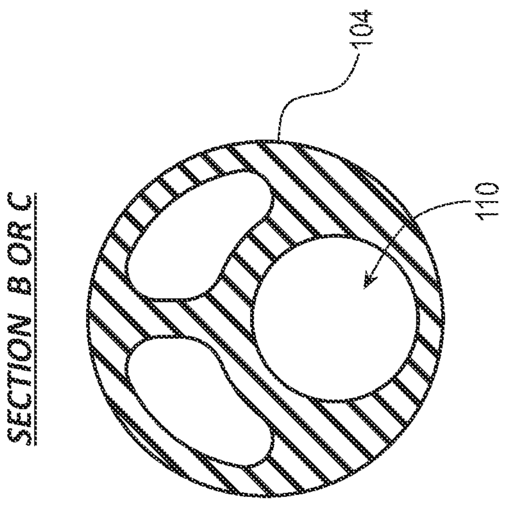
FIG. 4 illustrates a second or third transverse cross section of the catheter tube in accordance with some embodiments.
Figure 3:
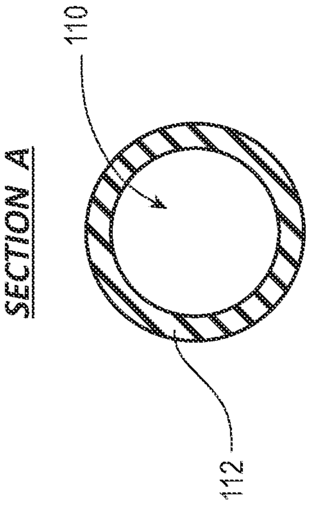
FIG. 3 illustrates a first transverse cross section of the catheter tube in accordance with some embodiments.

FIG. 1 illustrates a view of a catheter assembly 100 including a RICC 102 in accordance with some embodiments. FIG. 2 illustrates a distal portion of a catheter tube 104 of the RICC 102 in accordance with some embodiments. FIGS. 3 and 4 illustrate various transverse cross sections of the catheter tube 104 in accordance with some embodiments.

As shown the RICC 102 includes, in some embodiments, the catheter tube 104, a hub 106, and a number of extension legs 108 extending from the hub 106. The catheter tube 104, the hub 106, and the number of extension legs 108 are described in turn below.

The catheter tube 104 includes an introducing lumen 110 of a number of catheter-tube lumens. The introducing lumen 110 extends from a proximal end of the catheter tube 104 to a distal end of the catheter tube 104, which distal end of the catheter tube 104 corresponds with a distal end of a tip 112 of the RICC 102 in some embodiments. That is, in some embodiments, the tip 112 of the RICC 102 is formed of a distal-end portion of the catheter tube 104. In other embodiments, however, the tip 112 is formed separately and coupled to the distal end of the catheter tube 104. In such embodiments, the introducing lumen 110 further extends from the distal end of the catheter tube 104 to the distal end of the tip 112. Regardless, the catheter tube 104 is configured to accommodate an introducer needle, an introducer catheter, or an introducer combination thereof (i.e., the introducer catheter over the introducer needle) along the distal-end portion of the catheter tube 104 within the introducing lumen 110 and through the distal end of the catheter tube 104 or the tip 112 for introducing the RICC 102 into a blood vessel of a patient. The distal end of the catheter tube 104 or the tip 112 is configured to have an engineering fit such as a clearance fit (e.g., a free running, easy running, close running, sliding, or location clearance fit) or transition fit (e.g., a tight, similar, or fixed transition fit) with the introducer needle, the introducer catheter, or the introducer combination thereof in accordance with the International Organization for Standardization's ("ISO's") geometrical product specification for tolerances, specifically ISO 286. Such an engineering fit facilitates a smooth transition from the distal end of the catheter tube 104 or the tip 112 to the introducer needle, the introducer catheter, or the introducer combination thereof leaving little space for skin or other tissue to get caught between the distal end of the catheter tube 104 or the tip 112 and the introducer needle, the introducer catheter, or the introducer combination.

The catheter tube 104 can include a side opening 114 through a side of the catheter tube 104. When present, the side opening 114 is about 1-4 cm from the distal end of the catheter tube 104 or the tip 112 and opens into the introducing lumen 110 in the distal-end portion of the catheter tube 104. The catheter tube 104 is further configured to accommodate the introducer needle, the introducer catheter, or the introducer combination through the side opening 114, as well as along the distal-end portion of the catheter tube 104 within the introducing lumen 110, and through the distal end of the catheter tube 104 or the tip 112 for introducing the RICC 102 into the blood vessel of the patient.

Figure 5:
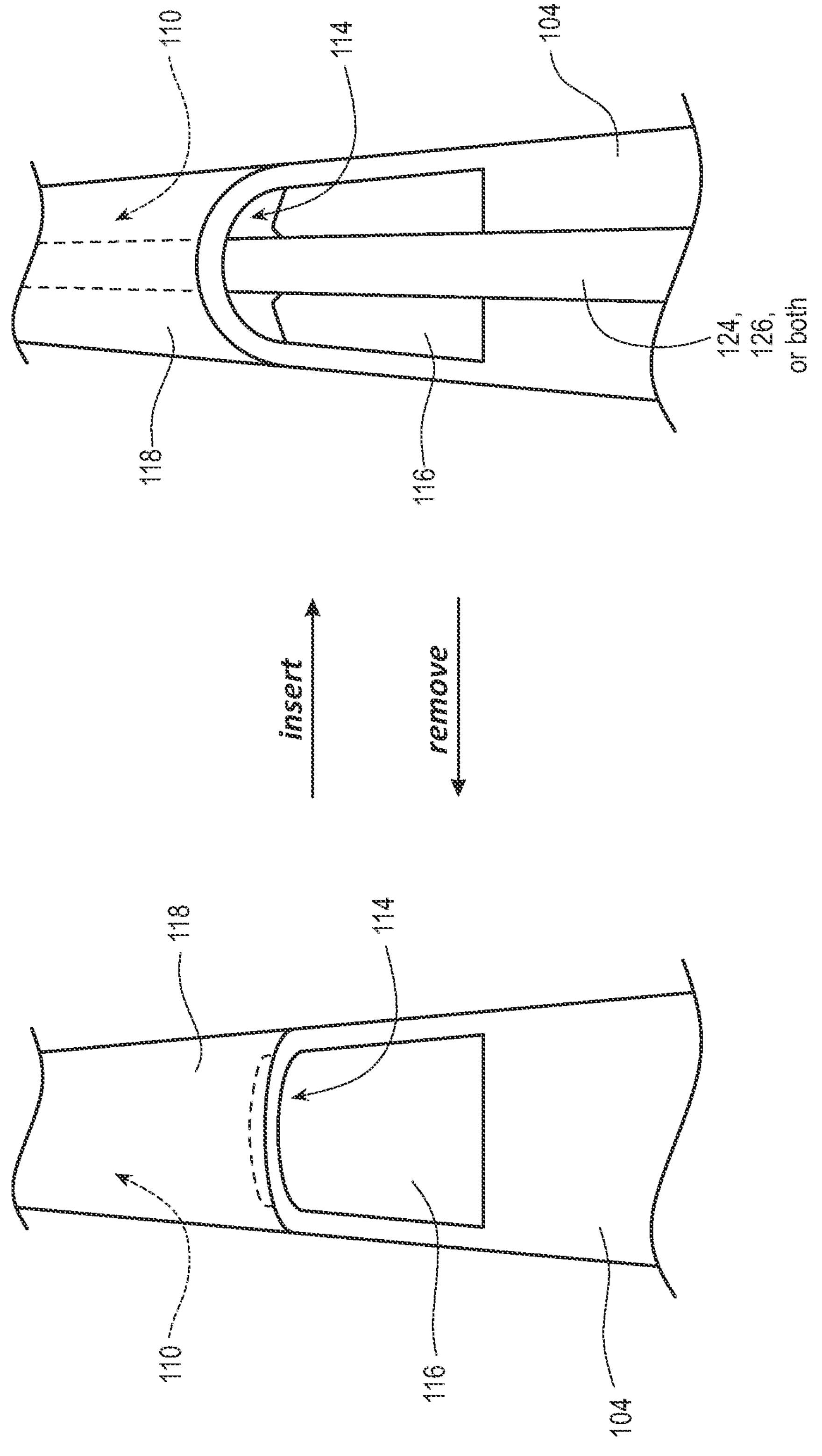
FIG. 5 illustrates a side opening in a side of the catheter tube in accordance with some embodiments.

FIG. 5 illustrates the side opening 114 in the side of the catheter tube 104 in accordance with some embodiments.

As shown, the side opening 114 can be a self-sealing side opening configured to seal when the introducer needle, the introducer catheter, or the introducer combination is removed from the RICC 102.

In an example, the catheter tube 104 can include a flap 116 (e.g., a small piece of elastomeric material adhered to the catheter tube 104) over the side opening 114, extending into the side opening 114, or both. The flap 116 is configured to be held open by the introducer needle, the introducer catheter, or the introducer combination. The flap 116 is configured to return to its default state when the introducer needle, the introducer catheter, or the introducer combination is removed from the side opening 114. The flap 116 seals the side opening 114 when returning to the default state.

In another example, the catheter tube 104 can include a puncture established by the introducer needle, the introducer catheter, or the combination thereof as the side opening 114. The catheter tube 104 around at least the side opening 114 (e.g., the puncture) is formed of an elastomeric material configured to return to its default state when the introducer needle, the introducer catheter, or the combination thereof is removed from the side opening 114. The catheter tube 104 around the side opening 114 (e.g., the puncture) seals the side opening 114 when returning to the default state. Alternatively or additionally, the catheter tube 104 can include the area or reinforcement 118 set forth below, which serves the same function as the catheter tube 104 around the side opening 114 (e.g., the puncture) being formed of an elastomeric material.

Notwithstanding the foregoing self-sealing embodiments of the side opening 114, the side opening 114 can be configured to remain open at all times, even when the introducer needle, the introducer catheter, or the introducer combination is removed from the side opening 114.

When the side opening 114 is not present, the medial-lumen opening 120 or the proximal-lumen opening 122 set forth below can be used for the introducer needle, the introducer catheter, or the introducer combination. Like that set forth above for the puncture established by the introducer needle, the introducer catheter, or the introducer combination as the side opening 114, the catheter tube 104 can include a puncture established by the introducer needle, the introducer catheter, or the introducer combination through a septum separating the distal lumen from the medial lumen or the proximal lumen via the medial-lumen opening 120 or the proximal-lumen opening 122. Again, the catheter tube 104 can be formed of an elastomeric material configured to return to its default state and seal when the introducer needle, the introducer catheter, or the combination thereof is removed from the puncture via the medial-lumen opening 120 or the proximal-lumen opening 122.

The catheter tube 104 can include an area of reinforcement 118 about the side opening 114. For example, the area of reinforcement 118 can be a segment of the catheter tube 104 that is slightly thicker, a segment of the catheter tube 104 of a different polymeric material such as a more durable or more elastomeric material, a band over the catheter tube 104 of a more durable or more elastomeric material, or the like. The area of reinforcement 118 is configured to maintain structural integrity of the catheter tube 104 about the side opening 114 such as when the introducer needle, the introducer catheter, or the combination thereof is disposed in the side opening 114 and the catheter assembly is being manipulated.

The hub 106 is coupled to a proximal-end portion of the catheter tube 104.

The hub 106 includes a suture wing with through holes for suturing the hub 106 to the patient.

The hub 106 includes a number of hub lumens equal in number to the number of catheter-tube lumens. Each hub lumen of the number of hub lumens is fluidly connected a catheter tube lumen of the number of catheter tube lumens.

The number of extension legs 108 extend from the hub 106. The number of extension legs 108 are equal in number to the number of hub lumens, which, in turn, are equal in number to the number of catheter-tube lumens. Each extension leg of the number of extension legs 108 includes an extension-leg lumen fluidly connected to a hub lumen of the number of hub lumens.

While the RICC 102 can include any number of lumens, the RICC 102 of FIGS. 1-4 is triluminal with three catheter-tube lumens, three hub lumens, and three extension-leg lumens. Indeed, the RICC 102 includes a set of three lumens including a distal lumen, a medial lumen, and a proximal lumen formed of fluidly connected portions of the three catheter-tube lumens, the three hub lumens, and the three extension-leg lumens. As shown, the distal lumen has a distal-lumen opening in a distal end of the RICC 102. The medial lumen has a medial-lumen opening 120 in the side of the catheter tube 104 proximal of the distal-lumen opening but distal of the side opening 114 when present. The proximal lumen has a proximal-lumen opening 122 in the side of the catheter tube 104 proximal of the medial-lumen opening 120 but distal of the side opening 114 when present. However, the RICC 102 is not limited to the foregoing arrangement of openings. Indeed, while the distal-lumen opening, the medial-lumen opening 120, and the proximal-lumen opening 122 are generally arranged as set forth, the side opening 114, when present, can be distal of the medial-lumen opening 120, between the medial-lumen opening 120 and the proximal-lumen opening 122, or proximal of the proximal-lumen opening 122 as shown.

Catheter Assemblies

FIG. 1 illustrates a view of the catheter assembly 100 including the RICC 102 in accordance with some embodiments.

As shown the catheter assembly 100 includes, in some embodiments, the RICC 102 and the introducer combination of an introducer needle 124 disposed in an introducer catheter 126, which introducer combination, in turn, is disposed in the side opening 114 of the catheter tube 104 of the RICC 102.

The catheter assembly 100 can further include a syringe 128. The syringe 128 includes a tip extending from a barrel of the syringe 128. The tip is configured as a Luer connector for connecting to a hub of the introducer needle 124, which hub is configured as a complementary Luer connector to that of the syringe 128.

The catheter assembly 100 can be packaged with the introducer combination disposed in the side opening 114 of the catheter tube 104 of the RICC 102 for immediate use once removed from a package containing the catheter assembly 100. Alternatively, the catheter assembly 100 can be packaged with the introducer combination separated from the RICC 102. Regardless, instructions for use can be included in the package for using the catheter assembly 100 including assembling the catheter assembly 100 (e.g., disposing the introducer combination in the catheter tube 104 of the RICC 102) if needed.

Methods

A method of the catheter assembly 100 or the RICC 102 thereof includes a method for inserting the RICC 102 into a blood-vessel lumen of a patient. Such a method includes, in some embodiments, a catheter assembly-obtaining step, a needle tract-establishing step, an introducer needle-removing step, an introducer catheter-advancing step, and a RICC-advancing step.

The catheter assembly-obtaining step includes obtaining the catheter assembly 100 including the RICC 102 and the introducer combination such as in or from a package thereof. As set forth above, the RICC 102 can include the catheter tube 104 with the side opening 114 through the side of the catheter tube 104 that opens into the introducing lumen 110. The introducer combination includes the introducer needle 124 disposed in the introducer-catheter lumen of the introducer catheter 126. The introducer combination can be disposed through the side opening 114 of the RICC 102, along the distal-end portion of the catheter tube 104 within the introducing lumen 110, and through the distal end of the catheter tube 104 or the tip 112.

If the catheter assembly 100 is not already assembled, the method can further include an introducer combination-disposing step of disposing the introducer combination in the side opening 114 of the catheter tube 104. Disposing the introducer combination in the side opening 114 of the catheter tube 104 can include establishing the side opening 114 of the catheter tube 104 with a tip of the introducer needle 124.

Whether the catheter assembly 100 is already assembled or not, the method can further include an introducer combination-adjusting step and a needle tip-ensuring step. The introducer combination-adjusting step includes adjusting the introducer combination such that at least about 1-7 cm of the introducer combination extends from the distal end of the RICC 102. (See, for example, FIG. 1.) The needle tip-ensuring step includes ensuring the tip of the introducer needle 124 extends past the distal end of the introducer catheter 126 before the needle tract-establishing step.

The needle tract-establishing step includes establishing a needle tract with the tip of the introducer needle 124 while the introducer combination is disposed in the RICC 102. Once established, the needle tract should extend from an area of skin to the blood-vessel lumen of the patient.

The method can further include a blood-aspirating step of aspirating blood with the syringe 128 fluidly connected to the introducer needle 124. The blood-aspirating step confirms the tip of the introducer needle 124 is disposed in the blood-vessel lumen before removing the introducer needle 124 from both the patient and the introducer combination.

Following the blood-aspirating step but before removing the introducer needle 124 from both the patient and the introducer combination, the method can further include a syringe-disconnecting step of disconnecting the syringe 128 from the hub of the introducer needle 124. Once the syringe 128 is disconnected from the hub of the introducer needle 124, an access guidewire can be advanced into the blood-vessel lumen through a needle lumen of the introducer needle 124 in an access-guidewire advancing step.

The introducer catheter-advancing step includes advancing the introducer catheter 126 into the blood-vessel lumen such as over the introducer needle 124, the access guidewire extending into the blood-vessel lumen from the needle lumen of the introducer needle 124, or a combination thereof. For example, the introducer catheter-advancing step includes advancing the introducer catheter 126 at least about 1-7 cm into the blood-vessel lumen. Advancing the introducer catheter at least about 1-7 cm into the blood-vessel lumen ensures the introducer catheter 126 is sufficiently disposed in the blood-vessel lumen before the RICC 102-advancing step.

The introducer needle-removing step includes removing the introducer needle 124 from both the patient and the introducer combination while leaving the introducer catheter 126 in place in both the patient and the RICC 102. If the access guidewire is advanced into the blood-vessel lumen in the access-guidewire advancing step, the introducer needle-removing step can include removing the access-guidewire as well.

The RICC-advancing step includes advancing the RICC 102 into the blood-vessel lumen over the introducer catheter 126 until the distal end of the RICC 102 is commensurate with a distal end of the introducer catheter 126, the RICC 102 is pushed off the introducer catheter 126, or the distal end of the RICC 102 is past the distal end of the introducer catheter 126 but not pushed off the introducer catheter 126.

With respect to advancing the RICC 102 into the blood-vessel lumen over the introducer catheter 126 until the distal end of the RICC 102 is commensurate with a distal end of the introducer catheter 126, the method can further subsequently include a first introducer catheter-removing step of removing the introducer catheter 126 from the RICC 102 through the side opening 114 through the side of the catheter tube 104. Once the introducer catheter 126 is removed from the RICC 102 through the side opening 114 of the catheter tube 104, the introducer catheter 126 can be completely removed from the blood-vessel lumen in a second introducer catheter-removing step of removing the introducer catheter 126 from the patient.

With respect to advancing the RICC 102 into the blood-vessel lumen over the introducer catheter 126 until the distal end of the RICC 102 is past the distal end of the introducer catheter 126 but not pushed off the introducer catheter in the RICC-advancing step, the method can also subsequently include the first introducer catheter-removing step of removing the introducer catheter 126 from the RICC 102 through the side opening 114 through the side of the catheter tube 104. Again, once the introducer catheter 126 is removed from the RICC 102 through the side opening 114 of the catheter tube 104, the introducer catheter 126 can be completely removed from the blood-vessel lumen in the second introducer catheter-removing step of removing the introducer catheter 126 from the patient.

However, with respect to advancing the RICC 102 into the blood-vessel lumen over the introducer catheter 126 until the RICC 102 is pushed off the introducer catheter 126, the first introducer catheter-removing step is not needed. Indeed, advancing the RICC 102 into the blood-vessel lumen over the introducer catheter until the RICC 102 is pushed off the introducer catheter simultaneously removes the introducer catheter 126 from the RICC 102 through the side opening 114 through the side of the catheter tube 104. Again, once the introducer catheter 126 is removed from the RICC 102 through the side opening 114 of the catheter tube 104, the introducer catheter 126 can be completely removed from the blood-vessel lumen in the second introducer catheter-removing step of removing the introducer catheter 126 from the patient.

The method can further include a maneuver guidewire-advancing step of advancing a maneuver guidewire into the blood-vessel lumen by way of, for example, the distal-lumen opening in the distal end of the RICC 102. The maneuver guidewire can be used to further advance the RICC 102 into the blood-vessel such as to the lower ⅓ of the superior vena cava ("SVC") of the heart before the maneuver guidewire is removed. As set forth above, the introducing lumen 110 from the distal-end portion of the catheter tube 104 through the distal end of the catheter tube 104 or the tip 112 is configured to accommodate the introducer needle, the introducer catheter, or the introducer combination. When that portion of the introducing lumen 110 includes the introducer needle, the introducer catheter, or the introducer combination, the introducer needle, the introducer catheter, or the introducer combination must be removed before the maneuver guidewire-advancing step to ensure the introducing lumen 110 is free of the introducer needle, the introducer catheter, or the introducer combination.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC"), comprising:

a catheter tube including:

an introducing lumen of a number of catheter-tube lumens, the introducing lumen extending from a proximal end of the catheter tube to a distal end of the catheter tube;

a number of lumen openings;

a self-sealing side opening proximal of the number of lumen openings, the self-sealing side opening through a side of the catheter tube that opens into the introducing lumen in a distal-end portion of the catheter tube, and the self-sealing side opening sealing when an introducer needle, an introducer catheter, or an introducer combination thereof is removed from the RICC by way of the self-sealing side opening; and a separately formed catheter tip coupled to the distal end of the catheter tube, the catheter tube configured to accommodate the introducer needle, the introducer catheter, or the introducer combination through the self-sealing side opening, along the distal-end portion of the catheter tube within the introducing lumen, and through the distal end of the catheter tube for introducing the RICC into a blood vessel of a patient;

a hub coupled to a proximal-end portion of the catheter tube including a number of hub lumens equal in number to the number of catheter-tube lumens; and a number of extension legs extending from the hub equal in number to the number of catheter-tube lumens, each extension leg of the number of extension legs including an extension-leg lumen.

2. The RICC of claim 1, wherein the self-sealing side opening is a puncture established by the introducer needle, the introducer catheter, or the introducer combination, the catheter tube around at least the puncture formed of an elastomeric material configured to return to its default state when the introducer needle, the introducer catheter, or the introducer combination is removed from the puncture, thereby sealing the puncture.

3. The RICC of claim 1, wherein the catheter tube includes a flap over the self-sealing side opening, extending into the self-sealing side opening, or both configured to be held open by the introducer needle, the introducer catheter, or the introducer combination and return to its default state when the introducer needle, the introducer catheter, or the introducer combination is removed from the self-sealing side opening, thereby sealing the self-sealing side opening.

4. The RICC of claim 1, wherein the catheter tube includes an area of reinforcement about the self-sealing side opening configured to maintain an integrity of the catheter tube about the self-sealing side opening.

5. The RICC of claim 1, wherein the number of catheter-tube lumens, the number of hub lumens, and a number of extension-leg lumens is three, the RICC including a set of three lumens including a distal lumen, a medial lumen, and a proximal lumen formed of fluidly connected portions of the number of catheter-tube lumens, the hub lumens, and the extension-leg lumens.

6. The RICC of claim 5, wherein the number of lumen openings is three, the distal lumen having a distal-lumen opening in a distal end of the RICC, the medial lumen having a medial-lumen opening in the side of the catheter tube distal of the self-sealing side opening, and the proximal lumen having a proximal-lumen opening in the side of the catheter tube distal of the self-sealing side opening but proximal of the medial-lumen opening.

7. The RICC of claim 4, wherein the area of reinforcement about the self-sealing side opening is a segment of the catheter tube that is slightly thicker than a remainder of the catheter tube.

8. The RICC of claim 4, wherein the area of reinforcement about the self-sealing side opening is a segment of the catheter tube that is of a different, more durable polymeric material than a remainder of the catheter tube.

9. The RICC of claim 4, wherein the area of reinforcement about the self-sealing side opening is a band over the catheter tube of a different, more durable polymeric material than a remainder of the catheter tube.

* * * * *